(12) United States Patent
Senaratne

(10) Patent No.: US 8,980,575 B2
(45) Date of Patent: Mar. 17, 2015

(54) PROCESS TO AVOID INHIBITION OF ACETOGENS BY CO

(71) Applicant: Ineos Bio SA, Lisle, IL (US)

(72) Inventor: Ryan Senaratne, Fayetteville, AR (US)

(73) Assignee: Ineos Bio SA, Rolle (CH)

( * ) Notice: Subject to any disclaimer, the term of this patent is extended or adjusted under 35 U.S.C. 154(b) by 0 days.

(21) Appl. No.: 14/018,487

(22) Filed: Sep. 5, 2013

(65) Prior Publication Data

US 2014/0080169 A1    Mar. 20, 2014

Related U.S. Application Data

(60) Provisional application No. 61/702,824, filed on Sep. 19, 2012, provisional application No. 61/702,826, filed on Sep. 19, 2012, provisional application No. 61/702,832, filed on Sep. 19, 2012, provisional application No. 61/702,837, filed on Sep. 19, 2012.

(51) Int. Cl.
*C12Q 1/02* (2006.01)
*B01D 51/00* (2006.01)

(52) U.S. Cl.
USPC .................................. 435/29; 95/11

(58) Field of Classification Search
USPC .................................. 435/29; 95/11
See application file for complete search history.

(56) References Cited

U.S. PATENT DOCUMENTS

| | | |
|---|---|---|
| 5,173,429 A | 12/1992 | Gaddy |
| 5,807,722 A | 9/1998 | Gaddy |
| 6,136,577 A | 10/2000 | Gaddy |
| 6,774,148 B2 | 8/2004 | O'Rear |
| 7,285,402 B2 | 10/2007 | Gaddy |
| 2012/0003706 A1* | 1/2012 | Hickey .......................... 435/140 |

FOREIGN PATENT DOCUMENTS

| | | |
|---|---|---|
| WO | WO 2011/139163 | 11/2011 |
| WO | WO 2012/015317 | 2/2012 |

OTHER PUBLICATIONS

Solubility of Gases in Water, Engineering Tool Box, http://www.engineeringtoolbox.com/gases-solubility-water-d_1148.html, 2007, printed from https://web.archive.org/web/20071023034530/http://www.engineeringtoolbox.com/gases-solubility-water-d_1148.html, on Oct. 24, 2014.*
Hurst, Kendall et al., "Carbon monoxide partial pressure effects on the metabolic process of syngas fermentation" Biochemical Engineering Journal, Sep. 22, 2009, 48(2010) 159-165.

(Continued)

*Primary Examiner* — Rosanne Kosson
(74) *Attorney, Agent, or Firm* — Ineos USA LLC

(57) ABSTRACT

A process is provided for fermenting CO-containing gaseous substrates. The process is effective for decreasing lag times and maintaining a culture in steady state by controlling CO concentration and minimizing effects of high or low CO concentrations during fermentation. The process includes providing syngas to a first fermentation zone, fermenting the syngas, and determining a CO concentration in a fermentation medium in the first fermentation zone. If the CO concentration in fermentation medium in the first fermentation zone has a calculated value of about 0.12 mM or greater, then at least a portion of the syngas being provided to the first fermentation zone is provided to one or more subsequent fermentation zones in an amount effective for providing a calculated CO concentration in any subsequent fermentation zone of about 0.12 mM or less.

25 Claims, 17 Drawing Sheets

(56) References Cited

OTHER PUBLICATIONS

Kundu, Suman et al. "Direct Measurement of Equilibrium Constants for High-Affinity Hemoglobins" Biophysical Journal, Jun. 2003, vol. 84 3931-3940.

Riggs, Seth et al. "Measuring Carbon Monoxide Gas-Liquid Mass Transfer in a Stirred Tank Reactor for Syngas Fermentation" Biotechnol, 2006, 22, 903-906.

* cited by examiner

PROCESS TO AVOID INHIBITION OF ACETOGENS BY CO

This application claims the benefit of U.S. Provisional Application Nos. 61/702,824, 61/702,826, 61/702,832 and 61/702,837, all filed on Sep. 19, 2012, all of which are incorporated in their entirety herein by reference.

A process is provided for fermenting CO-containing gaseous substrates. More specifically, the process includes determining CO concentration in a first fermentation medium in a first fermentation zone. If the CO concentration in the first fermentation medium has a calculated value of about 0.12 mM or greater, then at least a portion of the syngas provided to the first fermentation zone is provided to one or more subsequent fermentation zones in an amount effective for providing a calculated CO concentration in any subsequent fermentation zone of about 0.12 mM or less.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Many acetogenic microorganisms are poorly suited for industrial scale bioprocessing and have therefore not demonstrated commercial viability for this purpose. Such microorganisms have slow doubling time and low total productivities. In addition, many techniques for genetic manipulation (knockout, over-expression of transgenes via integration or episomic plasmid propagation) are inefficient, time-consuming, laborious, or non-existent.

Acetogenic microorganisms may be grown to produce ethanol from carbon monoxide. The growth process may involve culturing the acetogenic bacteria on increasing amounts of CO over time. Acetogenic microorganisms may be grown to produce ethanol from syngas that includes carbon monoxide. The growth process may involve culturing the acetogenic bacteria on increasing amounts of CO over time. High or low levels of CO in the fermentation may result in lower productivity

SUMMARY

A process is effective for maintaining high ethanol productivity levels during syngas fermentation. The process is effective for decreasing lag times and maintaining a culture in steady state by controlling CO concentration and minimizing effects of high or low CO concentrations during fermentation.

A syngas fermentation process includes providing syngas to a first fermentation zone, fermenting the syngas, and determining a CO concentration in a fermentation medium in the first fermentation zone. In accordance with the process, if the CO concentration in fermentation medium in the first fermentation zone has a calculated value of about 0.12 mM or greater, then at least a portion of the syngas being provided to the first fermentation zone is provided to one or more subsequent fermentation zones in an amount effective for providing a calculated CO concentration in any subsequent fermentation zone of about 0.12 mM or less.

In another aspect, a syngas fermentation process includes providing syngas to a first fermentor, fermenting the syngas, and determining a CO concentration in a fermentation medium in the first fermentor. In accordance with the process, if the CO concentration in fermentation medium in the first fermentor has a calculated value of about 0.12 mM or greater, then at least a portion of the syngas being provided to the first fermentor is provided to one or more subsequent fermentors in an amount effective for providing a calculated CO concentration in any subsequent fermentor of about 0.12 mM or less.

In another aspect, a fermentation process includes providing syngas to a fermentation medium in an amount effective for providing an initial calculated CO concentration in the fermentation medium of about 0.15 mM to about 0.70 mM. The process is effective for increasing cell density as compared to a starting cell density.

BRIEF DESCRIPTION OF FIGURES

The above and other aspects, features and advantages of several aspects of the process will be more apparent from the following figures.

Figure 1:
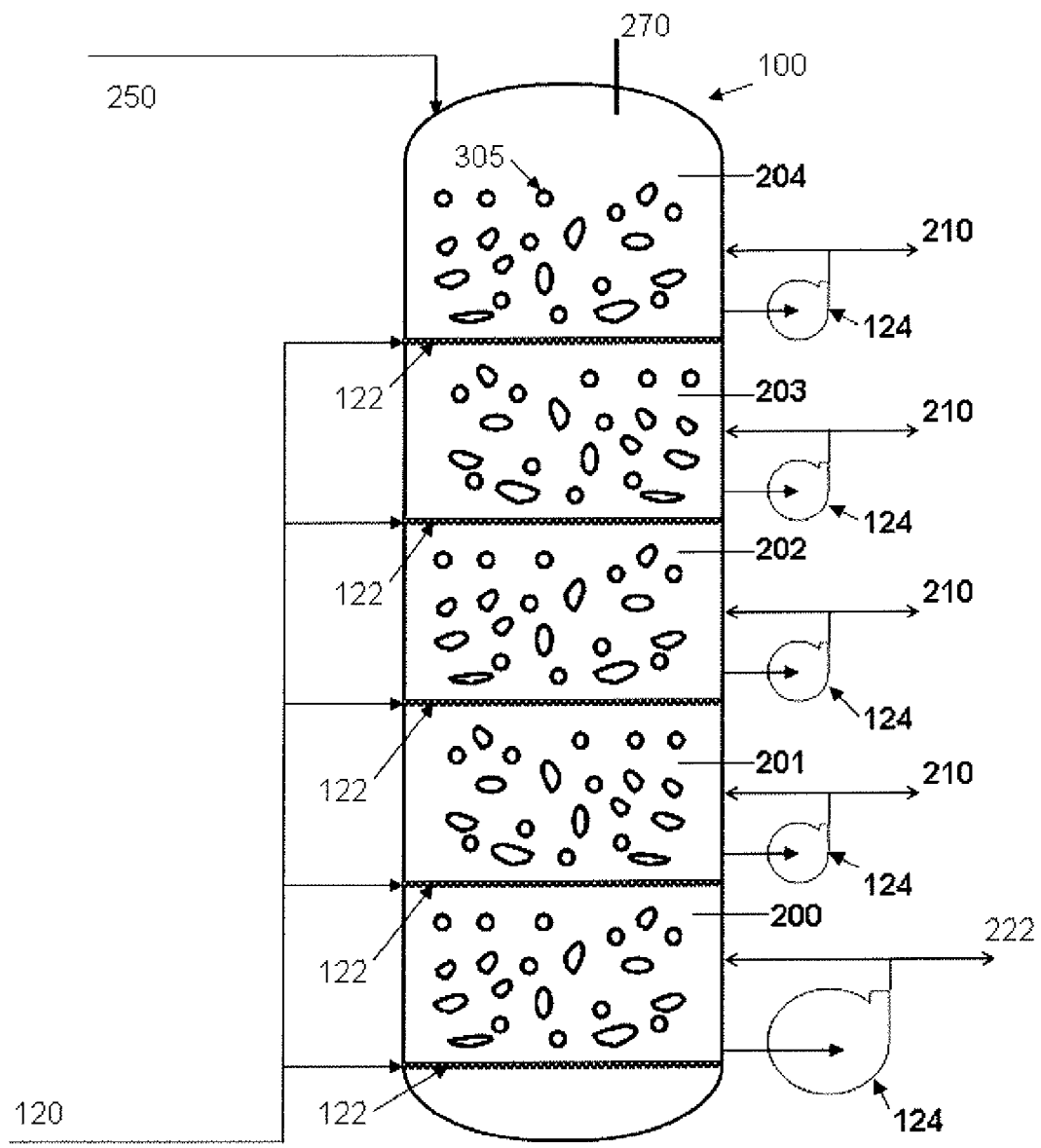
FIG. 1 is a perspective view of a fermentor with multiple fermentation zones.

Corresponding reference characters indicate corresponding components throughout the several views of the figures. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Control of CO concentrations in the fermentation through determining CO concentration in the fermentation medium is effective for providing high productivity levels. In this aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

Syngas

Syngas may be provided from any known source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

Depending on the syngas composition, the syngas may be provided directly to a fermentation process or may be further modified to include an appropriate $H_2$ to CO molar ratio. In one aspect, syngas provided to the fermentor has an $H_2$ to CO molar ratio of about 0.2 or more, in another aspect, about 0.25 or more, and in another aspect, about 0.5 or more. In another aspect, syngas provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

In one aspect, a fermentor design may include different fermentation zones in the same fermentor. For example, a large fermentor or a bubble column type reactor may include different fermentation zones. Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

As shown in FIG. 1, a fermentor 100 includes multiple fermentation zones 200. As shown, the fermentor 100 includes a first fermentation zone 200 and four additional fermentations zones 201, 202, 203, 204. In another aspect, the fermentor 100 may include two or more fermentation zones, and may includes from two to ten fermentation zones. A fermentation zone is defined as space above a gas inlet/sparger 122 and below the next gas/inlet sparger 122, or above a gas inlet/sparger 122 and the top of the fermentor 100. Medium, microbes and gases 305 in the fermentor 100 may flow between fermentation zones. The fermentor 100 may also include pumps 124. The pumps 124 may be used for product 222 removal and for removal of samples 210.

In one aspect, syngas enters the fermentor 100 through a syngas supply 120. The syngas supply 120 provides syngas to the gas inlet/spargers 122. Medium and nutrients may be supplied through medium/nutrient supply 250. Off-gas may exit the fermentor 100 through an off-gas port 270. Off-gas may be provided to a vent-gas boiler. The vent-gas boiler may be utilized to provide steam for energy production.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfbtomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

Upon reaching desired levels, liquid phase and cellular material is withdrawn from the reactor and replenished with medium. The process is effective for increasing cell density to about 2.0 grams/liter or more, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 6 grams/liter, and in another aspect, about 4 to about 5 grams/liter.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

In another aspect, the process is effective for maintaining a calculated CO concentration (mM) to cell density (grams/liter) ratio of about 0.001 to about 1.0. In another aspect, a calculated CO concentration to cell density ratio of about 0.01 to about 0.9, in another aspect, about 0.01 to about 0.8, in another aspect, about 0.02 to about 0.8, in another aspect, about 0.02 to about 0.75, in another aspect, about 0.03 to about 0.75, and in another aspect, about 0.03 to about 0.5.

In one aspect, syngas is supplied to a first fermentation zone 200. If a calculated CO concentration in the first fermentation zone 200 is about 0.12 mM or greater, then at least a portion of the syngas being supplied to the first fermentation zone 200 is provided to one or more subsequent fermentation zones through gas inlet/spargers 122. The portion of syngas provided to the one or more subsequent fermentation zones provides a calculated CO concentration in any subsequent fermentation zone of about 0.12 mM or less, in another aspect, about 0.10 mM or less, in another aspect, about 0.08 mM or less, in another aspect, about 0.06 mM or less, in another aspect, about 0.04 mM or less, and in another aspect, about 0.02 mM or less.

Syngas may be supplied to each fermentation zone one at a time or may be supplied to one or more fermentation zones simultaneously. In this aspect, syngas entering a fermentation zone will have about 20 mole % or more CO, in another aspect, about 30 mole % or more, in another aspect, about 40 mole % or more, and in another aspect, about 50 mole % or more.

In another aspect, syngas supplied to any fermentation zone will have an $H_2$ to CO molar ratio of about 0.2 or more, and from about 4 mole % to about 99.9 mole % CO. In another aspect, syngas entering any subsequent fermentation zone will have an $H_2$ to CO molar ratio of about 0.5 or more, in another aspect, about 1.0 or more, and in another aspect, about 3.5 or more.

Figure 2:
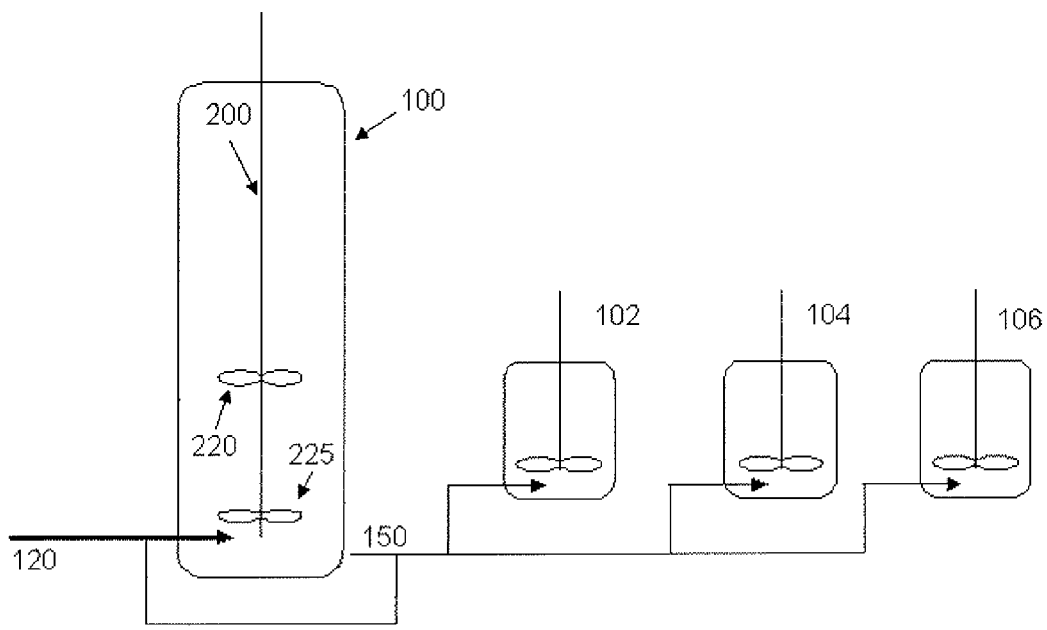
FIG. 2 is a perspective view of a series of fermentors.

Another aspect of a fermentor design is shown in FIG. 2. In this aspect, the design includes a first fermentor 100 connected in series to subsequent fermentors, such as for example, second fermentor 102, third fermentor 104, and fourth fermentor 106. The design may include any number of subsequent fermentors from 1 to about 10 (for example, 1, 2, 3, 4, 5, 6, 7, 8, 9 or 10 subsequent fermentors).

In one aspect, syngas enters the first fermentor 100 through a gas inlet/sparger 120. Dispersion of the syngas and further mixing is accomplished with at least one gas dispersion impeller 225 and at least one mixing impeller 220 which are coupled to a drive shaft 200.

Syngas 150 may be conveyed to one or more subsequent bioreactors. Syngas 150 may be supplied to each subsequent fermentor one at a time in series, or may be supplied to one or more subsequent fermentors simultaneously in parallel. In this aspect, the syngas entering any subsequent fermentor will have about 20 mole % or more CO, in another aspect, about 30 mole % or more, in another aspect, about 40 mole % or more, and in another aspect, about 50 mole % or more.

In another aspect, syngas supplied to any subsequent fermentor will have an $H_2$ to CO molar ratio of about 0.2 or more, and from about 4 mole % to about 99.9 mole % CO. In another aspect, syngas entering any subsequent fermentor will have an $H_2$ to CO molar ratio of about 0.5 or more, in another aspect, about 1.0 or more, and in another aspect, about 3.5 or more.

In another aspect, off-gas from a first or any subsequent fermentor may be provided to a vent-gas boiler. The vent-gas boiler may be utilized to provide steam for energy production.

Alcohol Productivity

Certain ratios of $H_2$ to CO and/or $CO_2$ to CO are effective for providing enhanced STY. In this aspect, the process is effective for providing a STY (space time yield) of about 1 gram or more total alcohol/(L·day). In another aspect, the process is effective for providing a providing a STY of at least about 10 g total alcohol/(L·day). Possible STY values include about 10 g total alcohol/(L·day) to about 300 g/(L·day), in another aspect, about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/(L·day), and in another aspect, about 40 g total alcohol/(L·day) to about 100 g total alcohol/(L·day).

As used herein, "total alcohol" includes ethanol, butanol, propanol and methanol. In one aspect, the total alcohol may include at least about 80 weight percent or more ethanol. In another aspect, total alcohol may include at least about 25 weight percent or less butanol.

In a related aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

Determination of CO Concentrations—Calculated Value

In order to calculate dissolved CO, the mass transfer coefficient (KLa) of the system needs to be determined. KLa value will depend on various factors, such as architecture of the reactor, superficial gas flow rate, un-aroused volume, temperature and agitation power. Therefore KLa values vary from reactor conditions to condition.

Henry's law: $P=K_H C$

Henry's constant=$K_H$=p/c (L(psi)/mol)

at 38° C., $K_H$=17640 (L(psi)/mol)

In a CSTR containing CO consuming bacteria, the following equation may be used to estimate dissolved CO.

KLa(($P_{CO}$(head space)/$K_H$)−($P_{CO}$(liquid)/$K_H$))=COU

COU=carbon monoxide uptake (mol/L/min)

KLa=mass transfer coefficient (min$^{-1}$)

($P_{CO}$(liquid)/$K_H$)=dissolved CO (mol/L)

When dissolved CO=0

KLa=COU/($P_{CO}$(head space)/$K_H$)

KLa(($P_{CO}$(head space)/$K_H$)−($P_{CO}$(liquid)/$K_H$))=COU $K_H$=L(psi)/mol

Determination of CO concentration by calculation is further illustrated in the Examples.

EXAMPLES

Example 1

Head-space partial pressure as a guide to provide feed-gas to the culture to avoiding CO inhibition with *Clostridium ljungdahlii* using a high CO feed-gas.

New Brunswick and CelliGen 310 bioreactors containing modified 1× ethanol medium were inoculated with 1.28 g/l of actively growing (in syngas) *Clostridium ljungdahlii*. Before inoculation, the rate of agitation of the reactor was set to 800 rpm. Gas and liquid samples taken from the reactor at every 1 to 4 hour intervals were analyzed for consumption or production of various gas components, broth acetic acid concentration, broth ethanol concentration and the optical density of the culture. Also the composition of the feed-gas was measured daily and the flow to the reactor was measured real time by the mass flow controller regulating feed-gas to the reactor. High CO composition feed gas of 95% CO/5% $N_2$ was utilized.

Figure 3:
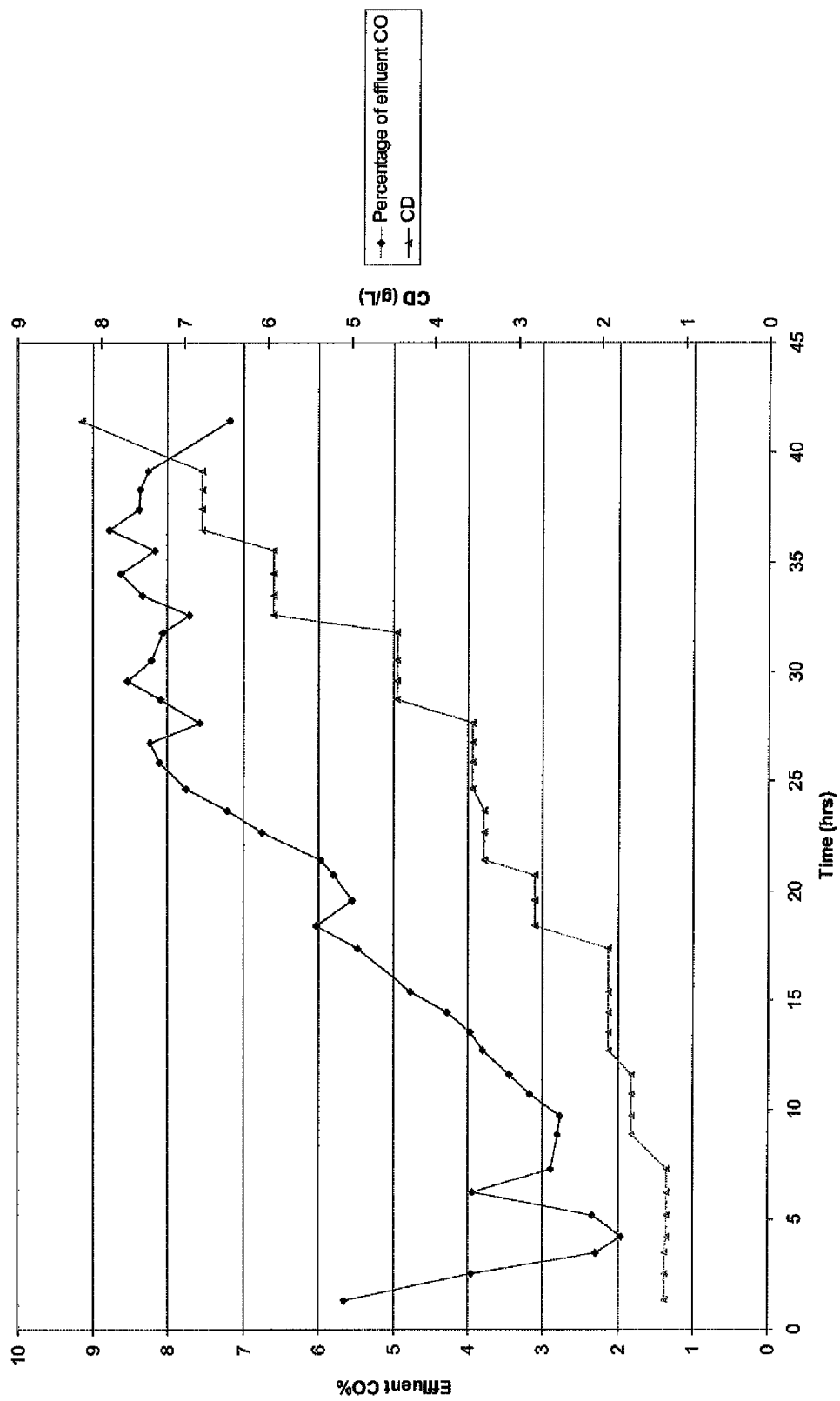
FIG. 3 illustrates the effect of controlling dissolved CO concentration by maintaining head-space CO partial pressure on *Clostridium ljungdahlii* cell mass using a high CO feed-gas.

The following method was used to regulate rate of gas supply to the reactor:

$X$=(head space CO %/100)×(measured reactor pressure(psig)+atmospheric pressure/atmospheric pressure(14.7))

if x is 0.08 or below gas flow to the reactor was increased by 7.6% of the current mole value of gas flow rate to the reactor if X is 0.12 or higher gas flow to the reactor was decreased by 7.6% of the current mole value of gas flow rate to the reactor The method was effective for maintaining the dissolved CO in the culture broth below 0.12 mmol/L at around 37 to 38° C. As shown in FIG. 3, cell mass increased with time and reached 8.24 g/L of cell mass within 41.4 hours after inoculation of the reactor. At this point culture was producing more than 12 g/L of ethanol.

A Shimadzu GC-2014 gas chromatograph was used to measure the broth ethanol and acetic acid concentrations. SRI 8610c gas chromatograph was used to measure the components of the feed-gas.

Example 2

Head-space partial pressure as a guide to provide feed-gas to the culture to avoiding CO inhibition with *Butyribacterium methylotrophicum* using a high CO feed-gas.

New Brunswick and CelliGen 310 reactor containing modified 1× ethanol medium were inoculated with 0.92 g/l of actively growing (in syngas) *Butyribacterium methylotrophicum*. Before inoculation, the rate of agitation of the reactor was set to 800 rpm. Gas and liquid samples taken from the reactor at every 1 to 4 hour intervals were analyzed for consumption or production of various gas components, broth acetic acid concentration, broth ethanol concentration and the optical density of the culture. Also the composition of the feed-gas was measured daily and the flow to the reactor was measured real time by the mass flow controller regulating feed-gas to the reactor. High CO composition feed gas of 95% CO/5% $N_2$ was utilized.

The method described in Example 1 was used to regulate the rate of gas supply to the reactor.

Figure 4:
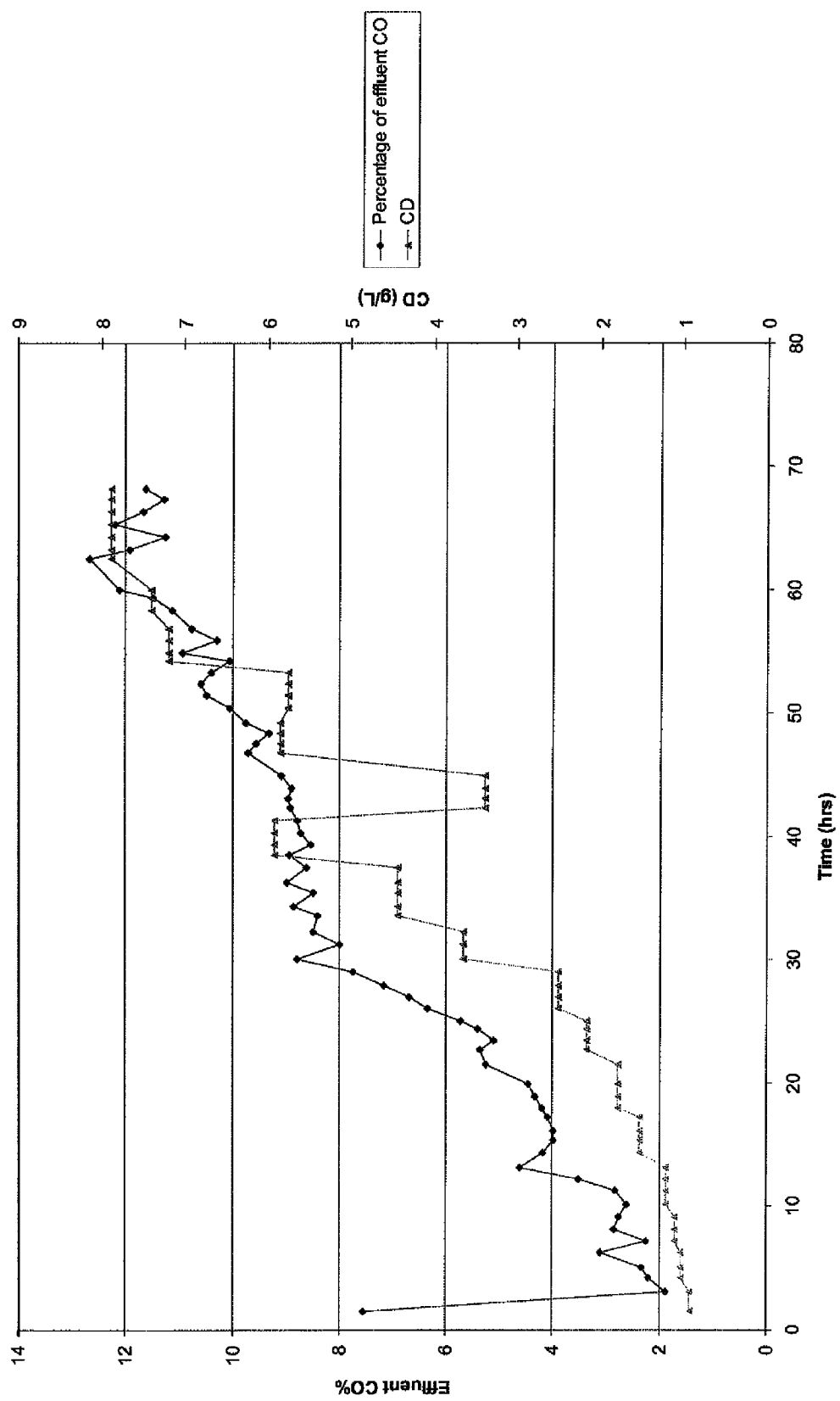
FIG. 4 illustrates the effect of controlling dissolved CO concentration by maintaining head-space CO partial pressure on *Butyribacterium methylotrophicum* cell mass using a high CO feed-gas.

As shown in FIG. 4, cell mass increased with time and reached 7.88 g/L of cell mass within 68 hours after inoculation of the reactor. At this point culture was producing 5 g/L of ethanol.

A Shimadzu GC-2014 gas chromatograph was used to measure the broth ethanol and acetic acid concentrations. SRI 8610c gas chromatograph was used to measure the components of the feed-gas.

Example 3

Use of low CO feed-gas to the culture to avoiding CO inhibition with *Clostridium ljungdahlii* using a low CO feed-gas.

New Brunswick and CelliGen 310 reactor containing modified 1× ethanol medium were inoculated with 0.38 g/l of actively growing (in syngas) *Clostridium ljungdahlii*. Before inoculation, the rate of agitation of the reactor was set to 800 rpm. Gas and liquid samples taken from the reactor at every 1 to 4 hour intervals were analyzed for consumption or production of various gas components, broth acetic acid concentration, broth ethanol concentration and the optical density of the culture. Also the composition of the feed-gas was measured daily and the flow to the reactor was measured in real time by the mass flow controller regulating feed-gas to the reactor.

A CO composition feed gas of 9.5% CO/90.5% $N_2$ was utilized and the flow was set to 534 ml/min. All through out the experiment the rate of feed gas to the reactor was not adjusted.

The method was utilized to keep the dissolved CO in the culture broth below 0.12 mmol/L at around 37 to 38° C. According to the Henry's Law, the maximum dissolved CO concentration that can be obtained by feeding a gas containing 9.5% is 0.079 mmol.

Figure 5:
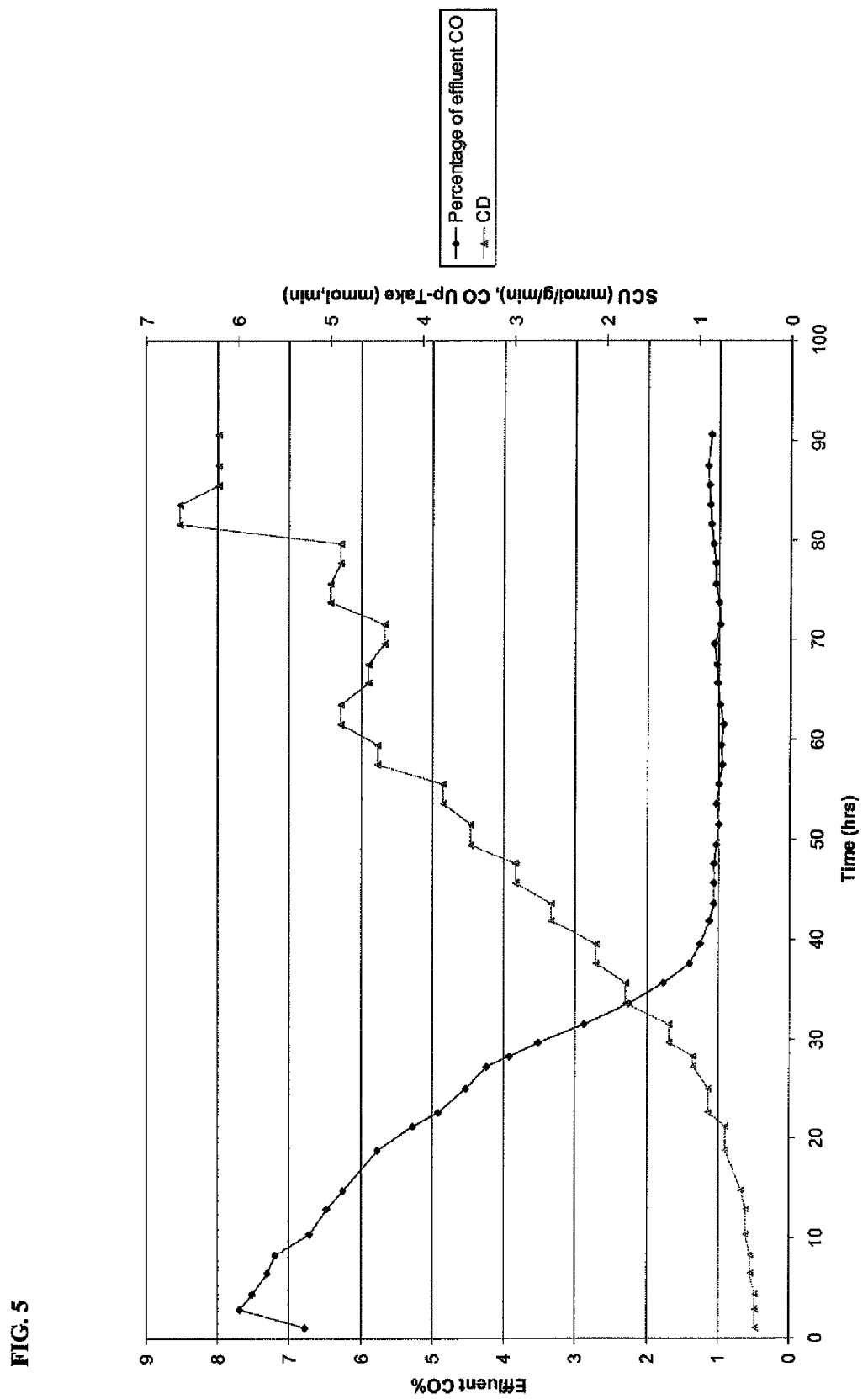
FIG. 5 illustrates the effect of CO concentration on *Clostridium ljungdahlii* cell mass using a low CO feed-gas.

As shown in FIG. 5, the cell mass increased with time and reached 6.21 g/l of cell mass within 90.6 hours after inoculation of the reactor. At this point culture was producing more than 5 g/L of ethanol.

A Shimadzu GC-2014 gas chromatograph was used to measure the broth ethanol and acetic acid concentrations. SRI 8610c gas chromatograph was used to measure the components of the feed-gas.

Example 4

Use of low CO feed-gas to avoid CO inhibition with *Butyribacterium methylotrophicum* using a low CO feed-gas.

New Brunswick and CelliGen 310 reactor containing modified 1× ethanol medium was inoculated with 0.86 g/l of actively growing (in 5% CO/95% N2) *Butyribacterium methylotrophicum*. At the start of the experiment the rate of agitation of the reactor was set to 800 rpm. Gas and liquid samples taken from the reactor at every 1 to 4 hour intervals were analyzed for consumption or production of various gas components, broth acetic acid concentration, broth ethanol concentration and the optical density of the culture. Also the composition of the feed-gas was measured daily and the flow to the reactor was measured real time by the mass flow controller regulating feed-gas to the reactor.

A CO composition feed gas of 9.5% CO/90.5% $N_2$ was utilized and the flow was set to 534 ml/min. All through out the experiment the rate of feed gas to the reactor was not adjusted.

This method was utilized to keep the dissolved CO in the culture broth below 0.12 mmol/l at around 37 to 38° C. According to the Henry's law the maximum dissolved CO concentration that can be obtained by feeding a gas containing 9.5% is 0.079 mmol.

Figure 6:
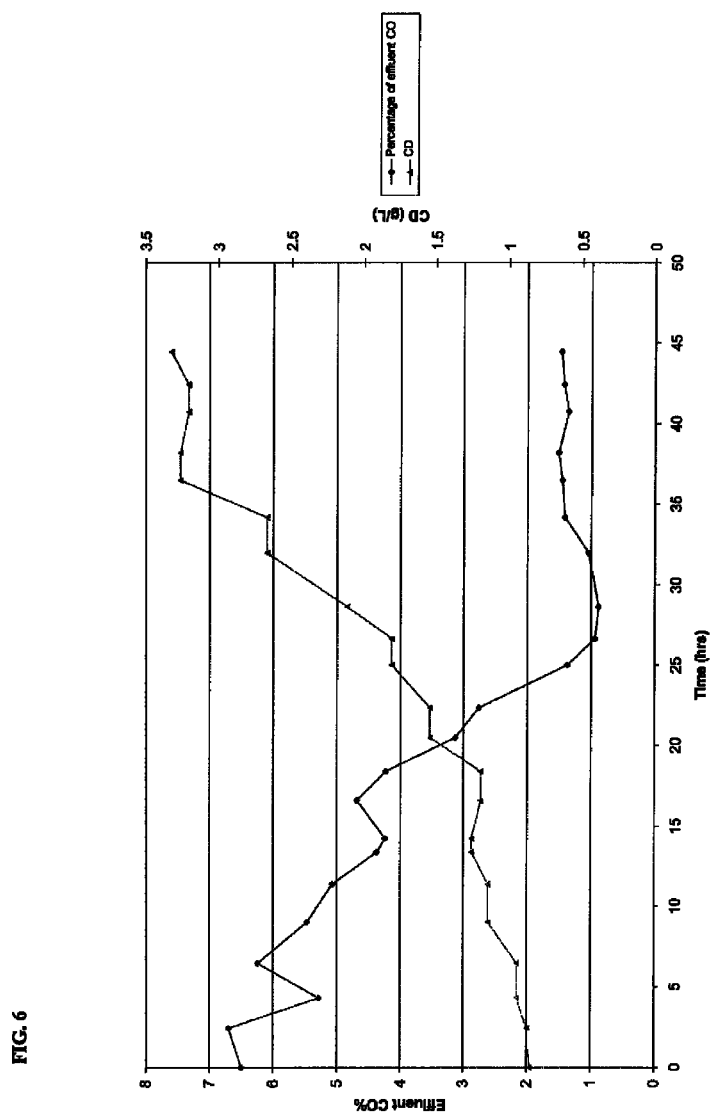
FIG. 6 illustrates the effect of CO concentration on *Butyribacterium methylotrophicum* cell mass using a low CO feed-gas.

As shown in FIG. 6 the cell mass increased with time and reached 3.32 g/L of cell mass within 44.4 hours after inoculation of the reactor. At this point culture was producing 3.7 g/L of ethanol.

A Shimadzu GC-2014 gas chromatograph was used to measure the broth ethanol and acetic acid concentrations. SRI 8610c gas chromatograph was used to measure the components of the feed-gas.

Example 5

Effect of CO Feed Rates on CO Conversion

*Clostridium ljungdahlii* was grown and maintained using only CO and $N_2$ (feed gas) in a bioreactor (New Brunswick BioFlo I or IIc). During the experiment, rate of feed gas was altered to obtain desired culture conversions. Lower culture conversions were employed to provide excess dissolved CO to *Clostridium ljungdahlii*.

Low culture conversions of CO was used as s method to provide excess dissolved CO to the culture. For example, when a culture in a reactor can convert X amount of CO at a given agitation and at a given flow rate, the dissolved CO can be increased by increasing the flow rate so that culture conversions go below X.

Figure 7:
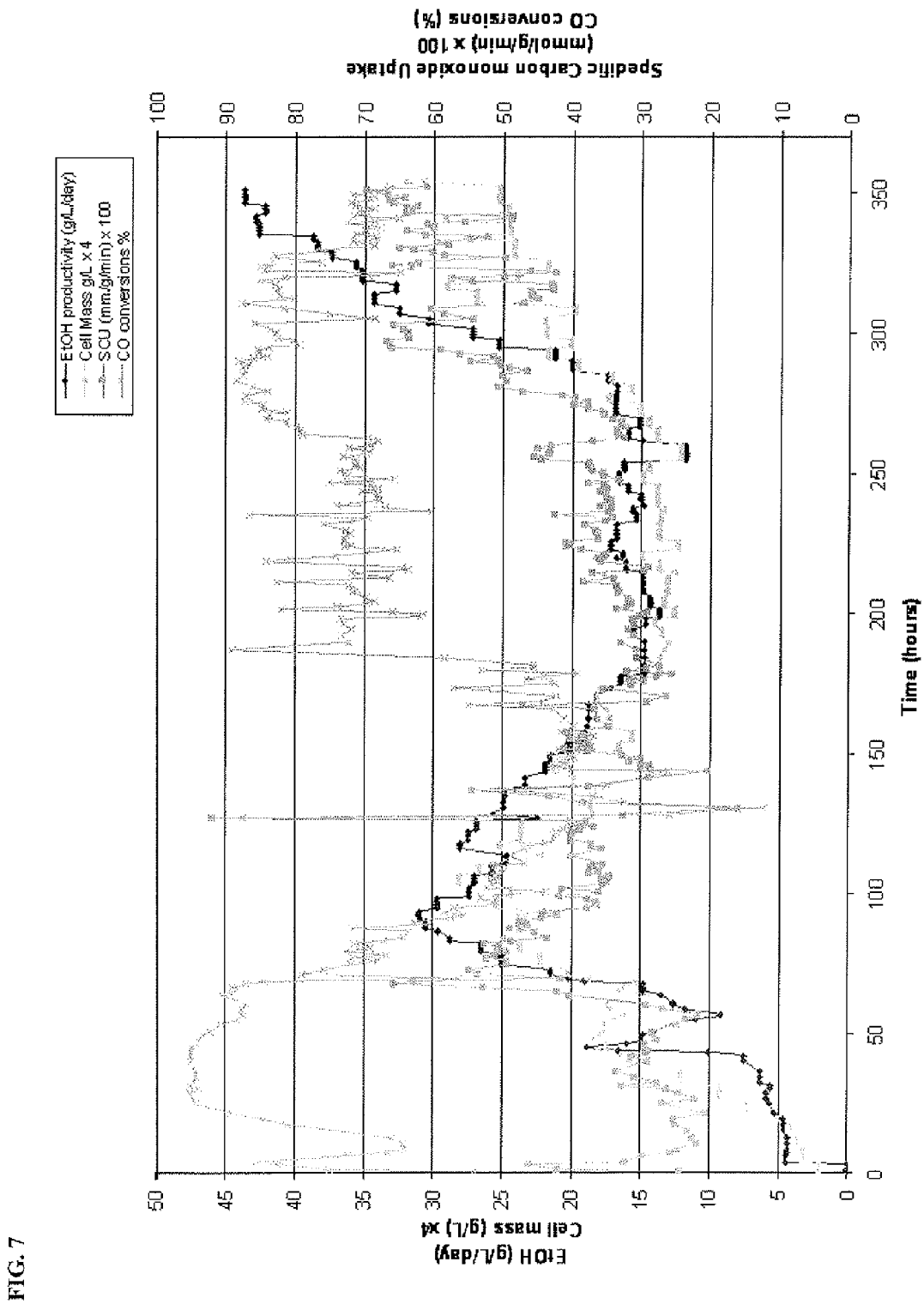
FIG. 7 shows the effect of CO feed rates on ethanol productivity, cell mass, CO conversion and specific CO uptake.

At approximately 80% CO conversions, *Clostridium ljungdahlii* didn't show signs of inhibition as determined through ethanol and acetic acid production, specific CO uptake (SCU), amount of cell mass, and cell morphology. *Clostridium ljungdahlii* was inhibited as feed gas was increased to maintain CO conversions to below approximately 70%. Culture was maintained at low acetic acid levels (<0.4 g/L) for at least 8 days. When CO conversions returned to approximately 80%, ethanol production, cell mass and typical morphology returned to healthy culture levels. Results are illustrated in FIG. 7.

Example 6

Inhibitory CO Feed Rates

*Clostridium ljungdahlii* was grown in a bioreactor (New Brunswick BioFlo I or IIc).

To achieve a conductivity of 9 mS/cm, a medium was made using 1.5× of all components except for vitamins. A four stage protocol was used as follows:

Stage 1: A culture was grown up in a 2 L bioreactor using syngas. With a cell density of 2.9 g/L, the gas source was switched from syngas mixture to a CO/$N_2$ mixture containing 95% CO and 5% $N_2$.

Stage 2: At T=26 hrs, a CO conversion target was set at >90%.

Stage 3: At T=70 hrs, the CO conversion target was decreased from 90% to 85%.

Stage 4: At T=97 hrs, the CO conversion target was decreased from 85% to 80%.

Dissolved CO was calculated for each gas sample using representative KLa values for a particular gas flow rate. These values were then averaged to find a representative value for each stage. Pictures were taken throughout the experiment in order to qualitatively study the morphology change over time.

Composition and concentrations (µM) of vitamin cocktail provided to the culture were as follows:

Biotin: 0.081863

Calcium Pantothenate: 0.115176

Thiamine: 0.148249

This vitamin cocktail was provided to the culture at a rate of about 0.12 µl/min/gram of cells in the culture.

CO concentrations were as follows:

|  | Stage 2: | Stage 3: | Stage 4: |
| --- | --- | --- | --- |
| Average Dissolved CO (Standard Deviation) | 0.04 mmol (0.0520) | 0.12 mmol (0.0366) | 0.29 mmol (0.1102) |
| SCU Average | 0.581 mmol/g/min | 0.559 mmol/g/min | 0.360 mmol/g/min |
| CRT Average | 23.74 hours | 31.89 hours | 75.92 hours |

Average cell retention time (CRT) was calculated for the period of 18 hours after the beginning of each stage to the end of each stage.

Culture was brought to steady state in Stage 1. The objective of the 2nd stage was to keep the dissolved CO level low by keeping the conversions high (>90%). Although the average dissolved CO in this stage was 0.0428 mmol/L, there were periods towards the second half of this stage where dissolve CO was as high as 0.14 to 0.17 mmol/L. These peaks of high dissolve CO coincide with the gas flow rate increments to the reactor.

The objective of Stage 3 was to obtain a step increment of dissolved CO in the reactor by maintaining lower level of bacterial conversion of CO. In this stage gas flow rate to the reactor was adjusted to maintain the culture conversion around 85%. With the above adjustments to the gas flow rate the average dissolved CO of the reactor was increased to 0.1221 mmol in the reactor. About 40 to 50% of disfigured bacteria were detected throughout this stage.

In stage 4 a further increment of average dissolved CO was obtained by adjusting the rate of gas flow to the reactor to maintain the bacterial conversions around 80%. The average dissolved CO in this stage was 0.2892 mmol. However, dissolved CO in the reactor in this stage included concentration gradient. The dissolved CO in the reactor rose to around 0.2 mmol once the conversions started to come down to 80%. At this point bacterial specific CO uptake (metabolism) proceeded on a downward trend. This downward trend of metabolism is indicative of bacteria entering into a negative feed back phase. For example, after a certain threshold point, bacterial metabolism started to get inhibited, this initial inhibition may have brought the threshold inhibitory dissolved CO concentration further down and caused further inhibition in the bacterial metabolism.

Example 7

Effect of CO Concentration on Growth

*Clostridium ljungdahlii* was grown in a bioreactor (New Brunswick BioFlo I or IIc). The following adjustments were made:

Conductivity of the culture was adjusted by adjusting the strength of the growth medium, for example concentration of all the components, except vitamin in the growth medium was increased by 1.5 times to increase the conductivity of the culture from approximately 7 mS to approximately 9.5 mS.

All experiments were started with the initial cell density of 0.38 (+/−0.02) or 0.48 g/L.

Initial gas flow rate of each experiment was kept unchanged throughout the experiment. Reactor parameters, when CO conversion values reach a plateau after a successful start-up, were used to calculate $K_{La}$ for relevant conditions.

Syngas composition was 30% CO, 15% $H_2$, 10% $CO_2$ and 45% $N_2$.

Figure 8:
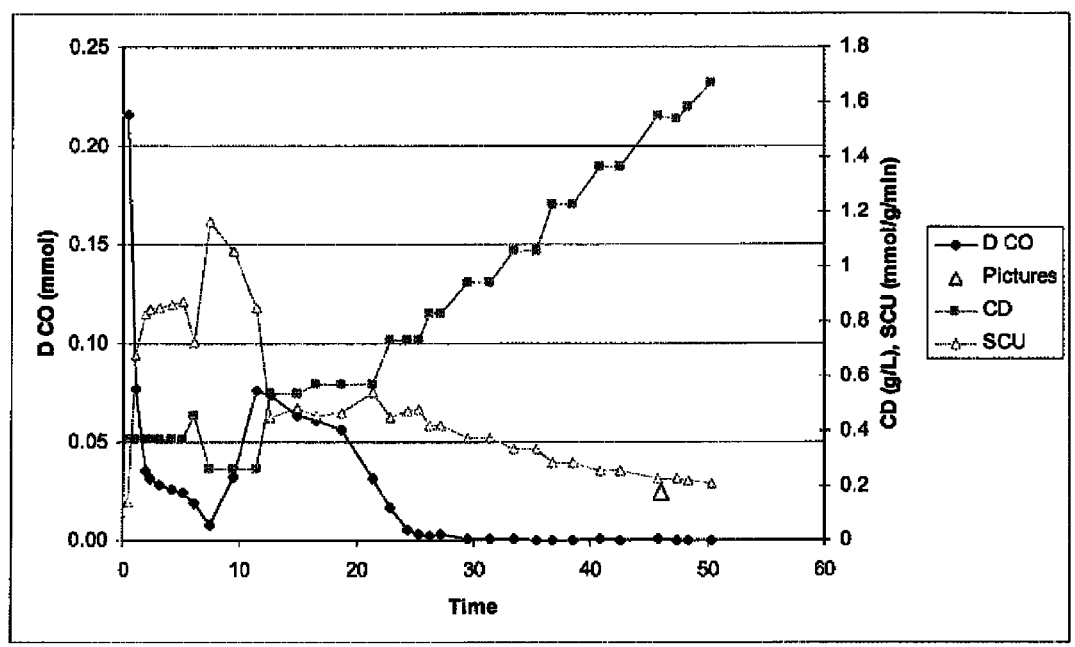
FIG. 8 illustrates growth of *Clostridium ljungdahlii* in 1× growth medium and a 25 ml/min syngas feed rate.

Bioreactor Run #1:
1× growth medium and 25 ml/min syngas feed rate was used in this experiment. As shown in FIG. 8, after an initial lag period of about 20 hours bacteria started to multiply at a doubling time of about 20 hours. Maximum calculated dissolved CO was about 0.08 mmol in the reactor broth. (D CO: dissolved CO concentration in the reactor broth, CD: cell density, SCU specific CO uptake.)

Figure 9:
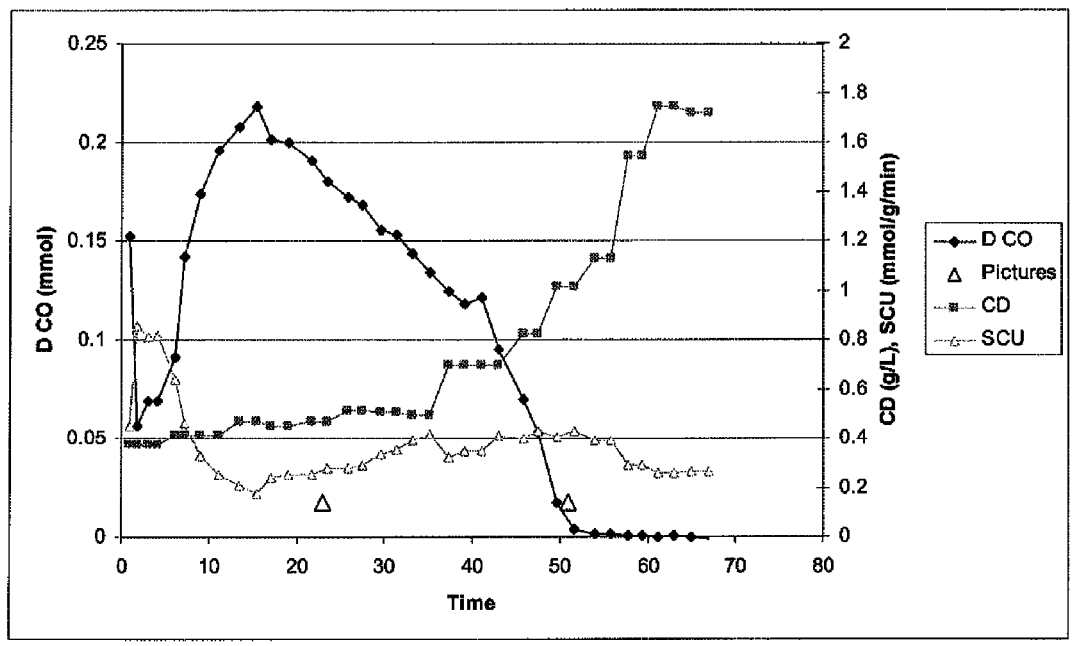
FIG. 9 illustrates growth of *Clostridium ljungdahlii* in 1× growth medium and a 35 ml/min syngas feed rate.

Bioreactor Run #2:
1× growth medium and 35 ml/min syngas feed rate was used in this experiment. As shown in FIG. 9, after an initial lag period of about 36 hours bacteria started to multiply at a doubling time of about 20 hours. Maximum calculated dissolved CO was about 0.22 mmol in the reactor broth. At about 51 hours after inoculation, cells became elongated and curved.

Figure 10:
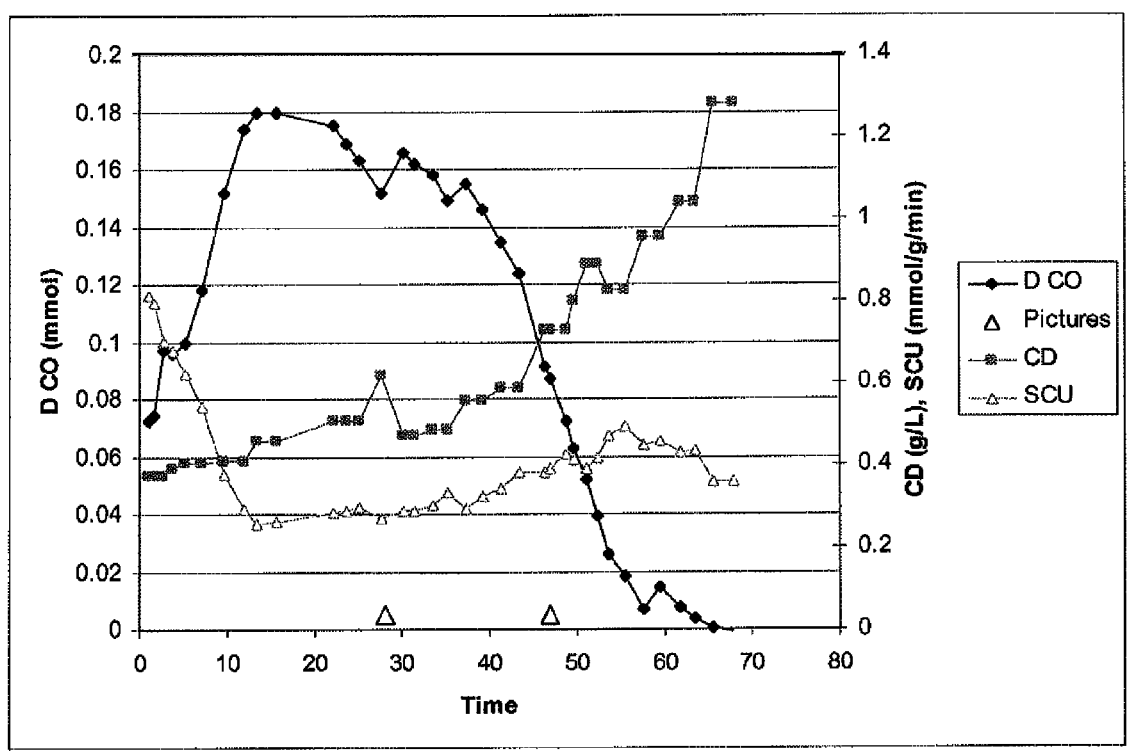
FIG. 10 illustrates growth of *Clostridium ljungdahlii* in 1× growth medium and a 40 ml/min syngas feed rate.

Bioreactor Run #3:
1× growth medium and 40 ml/min syngas feed rate was used in this experiment. As shown in FIG. 10, after initial lag period of about 45 hours bacteria started to multiply at a doubling time of about 20 hours. Maximum calculated dissolved CO was about 0.22 mmol in the reactor broth. At about 51 hours after inoculation, cells became elongated and curved.

Figure 11:
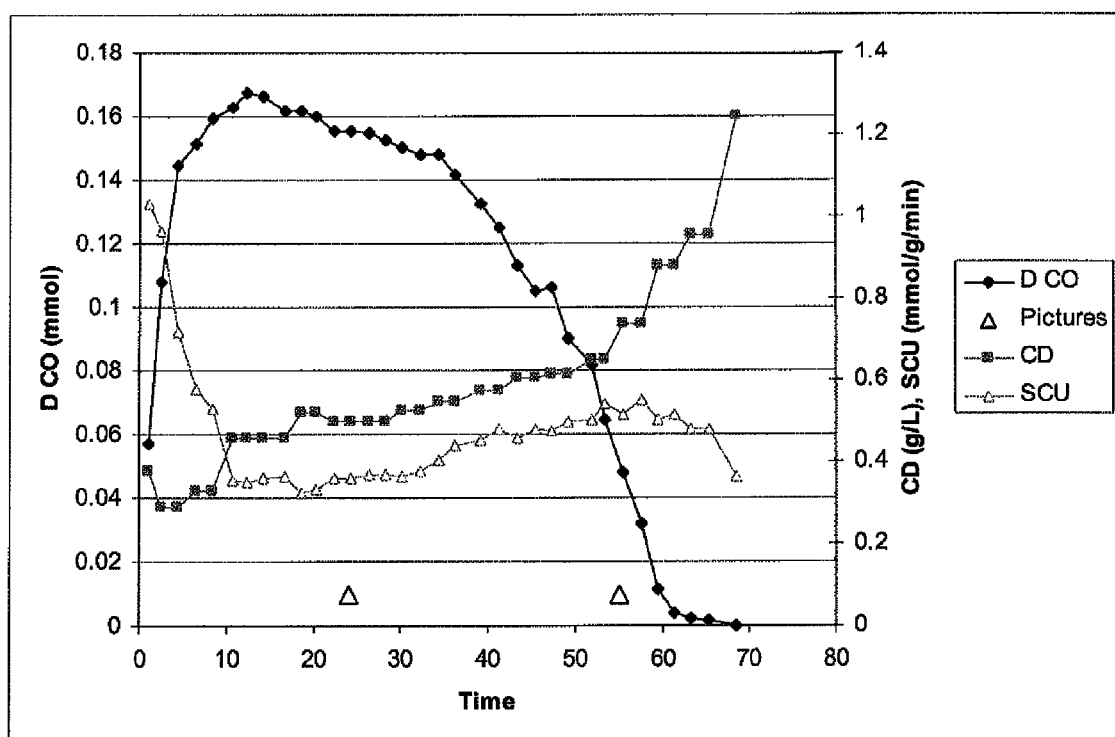
FIG. 11 illustrates growth of *Clostridium ljungdahlii* in 1× growth medium and a 45 ml/min syngas feed rate.

Bioreactor Run #4:
1× growth medium and 45 ml/min syngas feed rate was used in this experiment. As shown in the FIG. 11, after initial lag period of about 50 hours bacteria started to multiply at a doubling time of about 20 hours. Maximum calculated dissolved CO was about 0.17 mmol in the reactor broth. At about 55 hours after inoculation, cells became elongated and curved.

Figure 12:
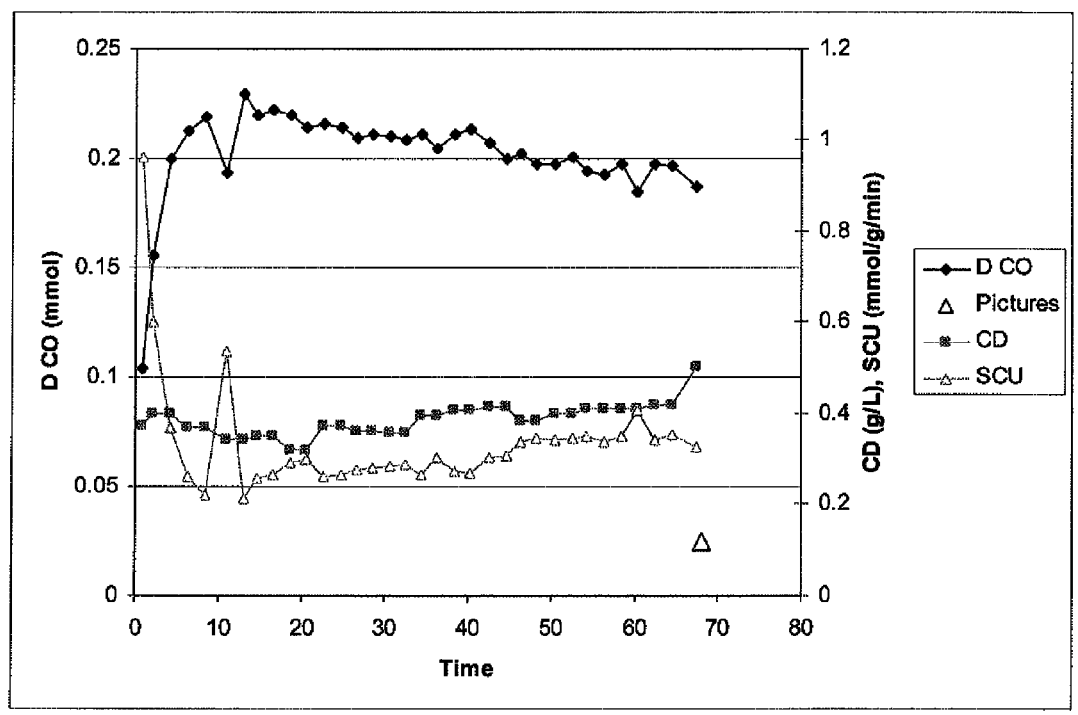
FIG. 12 illustrates growth of *Clostridium ljungdahlii* in 1× growth medium and a 50 ml/min syngas feed rate.

Bioreactor Run #5:
1× growth medium and 50 ml/min syngas feed rate was used in this experiment. As shown in the FIG. 12, culture continued to lag even at about 70 hours after the inoculation. Maximum calculated dissolved CO was around 0.23 mmol in the reactor broth.

Figure 13:
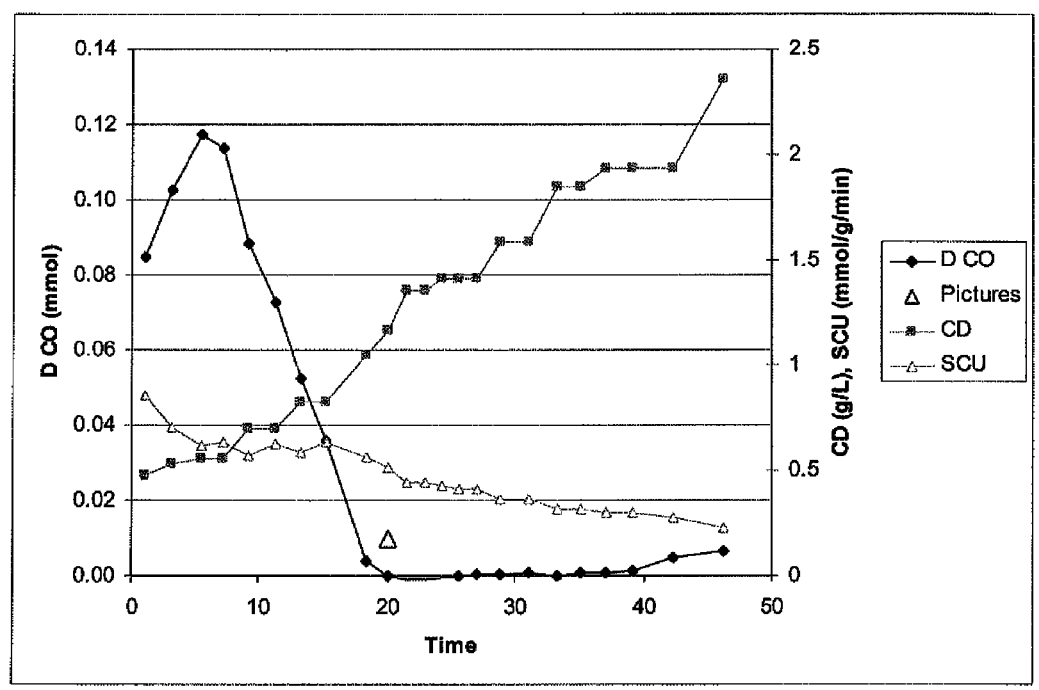
FIG. 13 illustrates growth of *Clostridium ljungdahlii* in 1× growth medium and a 50 ml/min syngas feed rate with a higher initial inoculum.

Bioreactor Run #6:
1× growth medium and 50 ml/min syngas feed rate was used in this experiment. This experiment was started with higher inoculum of bacteria compared to all above experiments (4.8 vs 3.8 g/L cells). As shown in FIG. 13, after an initial lag period of about 10 hours bacteria started to multiply at a doubling time of about 20 hours. Maximum calculated dissolved CO was about 0.12 mmol in the reactor broth. At about 20 hours after inoculation, cell morphology was short and consistent in nature.

Figure 14:
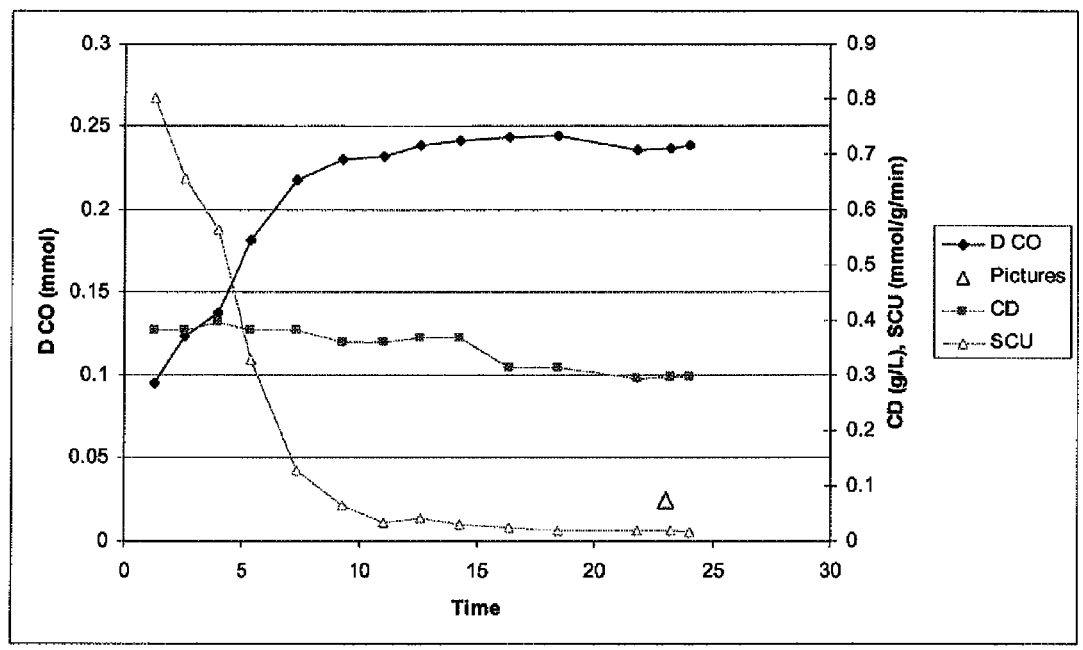
FIG. 14 illustrates growth of *Clostridium ljungdahlii* in 1.5× growth medium and a 45 ml/min syngas feed rate with a higher initial inoculum.

Bioreactor Run #7:
1.5× growth medium and 45 ml/min syngas feed rate was used in this experiment. This experiment was started with an inoculum of 3.8 g/L of bacteria. As shown in FIG. 14, bacterial cell density went down with time. Maximum calculated dissolved CO was about 0.25 mmol in the reactor broth.

Figure 15:
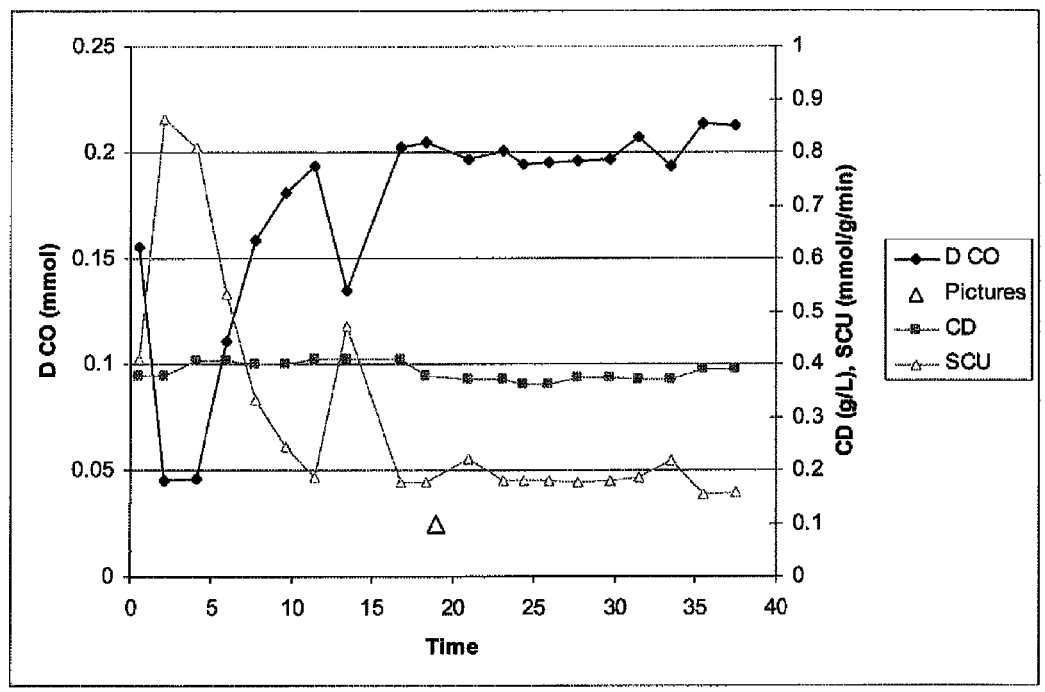
FIG. 15 illustrates growth of *Clostridium ljungdahlii* in 1.5× growth medium and a 35 ml/min syngas feed rate with a higher initial inoculum.

Bioreactor Run #8:
1.5× growth medium and 35 ml/min syngas feed rate was used in this experiment. This experiment was started with an inoculum of 3.8 g/L of bacteria. As shown in FIG. 15, bacterial cell density went down with time. Maximum calculated dissolved CO was about 0.22 mmol in the reactor broth.

Figure 16:
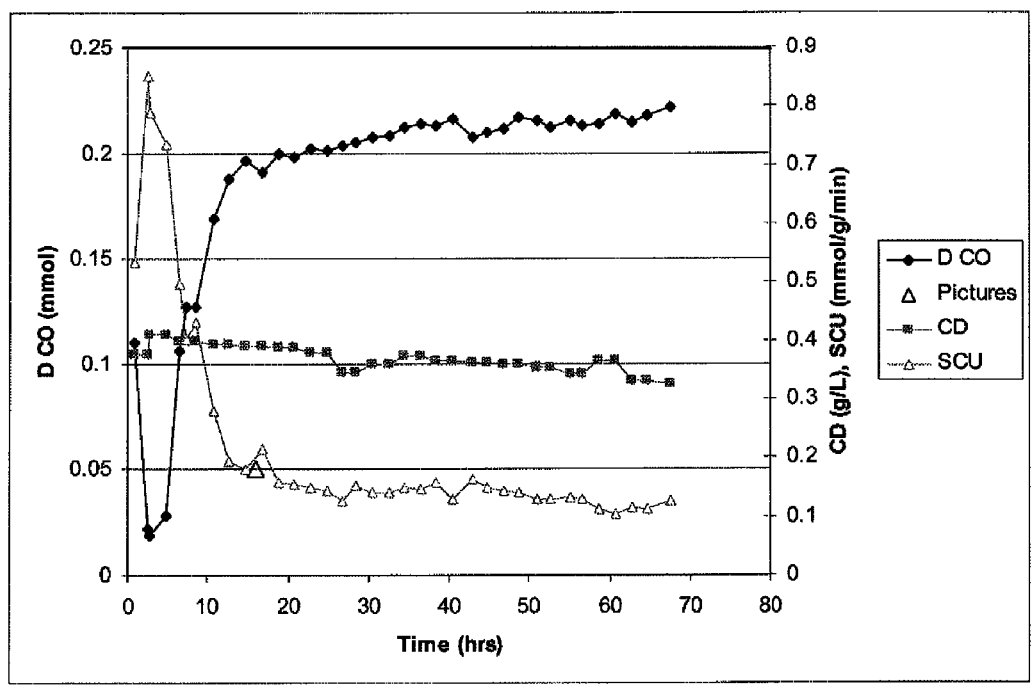
FIG. 16 illustrates growth of *Clostridium ljungdahlii* in 1.5× growth medium and a 30 ml/min syngas feed rate with a higher initial inoculum.

Bioreactor Run #9:
1.5× growth medium and 30 ml/min syngas feed rate was used in this experiment. This experiment was started with an inoculum of 3.8 g/L of bacteria. As shown in FIG. 16, bacterial cell density went down with time. Maximum calculated dissolved CO was about 0.22 mmol in the reactor broth.

Figure 17:
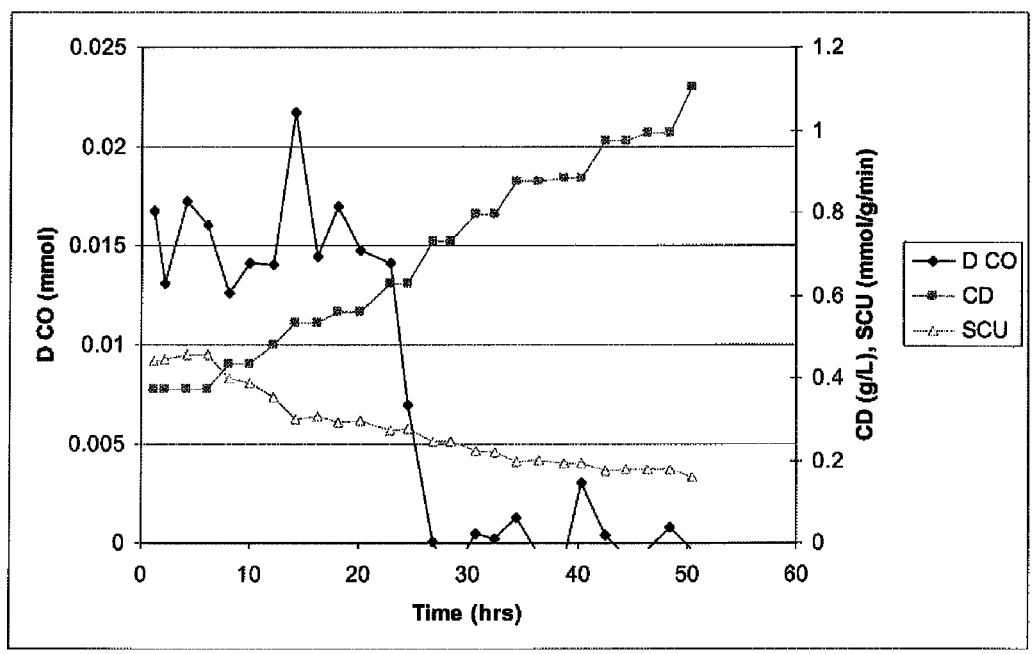
FIG. 17 illustrates growth of *Clostridium ljungdahlii* in 1.5× growth medium and a 20 ml/min syngas feed rate with a higher initial inoculum.

Bioreactor Run #10:
1.5× growth medium and 20 ml/min syngas feed rate was used in this experiment. This experiment was started with an inoculum of 3.8 g/L of bacteria. As shown in FIG. 17, bacterial cell density went up with time and achieved a 20 hour doubling time. Maximum calculated dissolved CO was around 0.022 mmol in the reactor broth.

While the invention herein disclosed has been described by means of specific embodiments, examples and applications thereof, numerous modifications and variations could be made thereto by those skilled in the art without departing from the scope of the invention set forth in the claims.

What is claimed is:

1. A method for reducing growth inhibition by carbon monoxide (CO) of microbes in fermentation, comprising:
   a) providing syngas to a first fermentation zone;
   b) fermenting the syngas; and
   c) determining the CO concentration in the fermentation medium in the first fermentation zone, wherein if the CO concentration in the fermentation medium in the first fermentation zone has a calculated value of 0.12 mM or greater, then at least a portion of the syngas being provided to the first fermentation zone is provided to one or more subsequent fermentation zones in an amount effective for providing a calculated CO concentration in the first fermentation zone of at least 0.12 mM or less.

2. The process of claim 1 wherein CO concentration is calculated by determining a supply factor, wherein the supply factor=(head space CO %÷100)×(((measured reactor pressure (psig)+atmospheric pressure))÷(atmospheric pressure× 14.7)).

3. The process of claim 1 wherein the syngas provided to the first or any subsequent fermentation zone has a molar ratio of $H_2$ to CO of 0.2 or more.

4. The process of claim 1 wherein the syngas provided to the first or any subsequent fermentation zone has 40 mole percent or more of CO plus $H_2$ and an $H_2$ content of 30 mole percent or less.

5. The process of claim 1 wherein the syngas provided to the first or any subsequent fermentation zone has a $CO/CO_2$ molar ratio of at least 0.75.

6. The process of claim 1 wherein the process is effective for increasing cell density to 2.0 g/L or more in the first or any subsequent fermentation zone.

7. The process of claim 1 wherein the process provides a calculated CO concentration to initial cell density ratio of about 0.5 to about 0.9.

8. The process of claim 1 wherein the fermentation medium includes microbes capable of consuming and/or producing CO.

9. The process of claim 8 wherein the microbes are acetogenic bacteria.

10. The process of claim 9 wherein the acetogenic bacteria are selected from the group consisting of *Acetogenium kivui, Acetoanaerobium noterae, Acetobacterium woodii, Alkalibaculum bacchi* CP11 (ATCC BAA-1772), *Blautia producta, Butyribacterium methytotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum* P262, *Clostridium autoethanogenum, Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Ctostridium carboxidivorans* P7 (ATCC PTA-7827), *Clostridium coskatii* (ATCC PTA-10522), *Ctostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Ctostridium thermoaceticum, Ctostridium ultunense, Desulfotomaculum kuznetsovii, Eubacterium limosum, Geobacter sulfurreducens, Methanosarcina acetivorans, Methanosarcina barkeri, Morrella thermoaeetica, Morrella thermoautotrophica, Oxobacter pfennigii, Peptostreptococcus productus, Ruminococcus productus, Thermoanaerobacter kivui* and mixtures thereof.

11. A method for reducing growth inhibition by carbon monoxide (CO) of microbes in fermentation, comprising:
    a) providing syngas to a first fermentor;
    b) fermenting the syngas; and
    c) determining the CO concentration in the fermentation medium in the first fermentor, wherein if the CO concentration in the fermentation medium in the first fermentor has a calculated value of 0.12 mM or greater, then at least a portion of the syngas being provided to the first fermentor is provided to one or more subsequent fermentors in an amount effective for providing a calculated CO concentration in the first fermentor of at least 0.12 mM or less.

12. The process of claim 11 wherein CO concentration is calculated by determining a supply factor, wherein the supply factor=(head space CO %÷100)×(((measured reactor pressure (psig)+atmospheric pressure))÷(atmospheric pressure× 14.7)).

13. The process of claim 11 wherein the syngas provided to the first or any subsequent fermentation zone has a molar ratio of $H_2$ to CO of 0.2 or more.

14. The process of claim 11 wherein the syngas provided to the first or any subsequent fermentation zone has 40 mole percent or more of CO plus $H_2$ and an $H_2$ content of 30 mole percent or less.

15. The process of claim 11 wherein the syngas provided to the first or any subsequent fermentation zone has a CO/OO$_2$ molar ratio of at least 0.75.

16. The process of claim 11 wherein the process is effective for increasing cell density to 2.0 g/L or more in the first or any subsequent fermentation zone.

17. The process of claim 11 wherein the process is effective for maintaining a calculated CO concentration to cell density ratio of about 0.001 to about 1.0.

18. The process of claim 11 wherein the fermentation medium includes microbes capable of consuming and/or producing CO.

19. The process of claim 18 wherein the microbes are acetogenic bacteria.

20. The process of claim 19 wherein the acetogenic bacteria are selected from the group consisting of *Acetogenium kivui, Acetoanaerobium noterae, Acetobacterium woodii, Alkalibaculum bacchi* CP11 (ATCC BAA-1772), *Blautia producta, Butyribacterium methytotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum* P262, *Clostridium autoethanogenum, Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Ctostridium carboxidivorans* P7 (ATCC PTA-7827), *Clostridium coskatii* (ATCC PTA-10522), *Ctostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Ctostridium thermoaceticum, Ctostridium ultunense, Desulfotomaculum kuznetsovii, Eubacterium limosum, Geobacter sulfurreducens, Methanosarcina acetivorans, Methanosarcina barkeri, Morrella thermoaeetica, Morrella thermoautotrophica, Oxobacter pfennigii, Peptostreptococcus productus, Ruminococcus productus, Thermoanaerobacter kivui* and mixtures thereof.

21. The process of claim 11 wherein syngas is provided to subsequent fermentors operating in parallel.

22. The process of claim 11 wherein syngas is provided to subsequent fermentors operating in series.

23. The process of claim 11 wherein the first or subsequent fermentors are different fermentation zones in the fermentor.

24. The process of claim 11 wherein at least a portion of off-gas from a first or any subsequent fermentor is provided to a vent-gas boiler.

25. A method for reducing growth inhibition by carbon monoxide (CO) of microbes in fermentation, comprising
    a) providing syngas to a fermentation medium in an amount effective for providing an initial calculated CO concentration in the fermentation medium of about 0.15 mM to about 0.70 mM, wherein the method is effective for increasing cell density of the microbes as compared to the same method in which the concentration of CO is not controlled.

* * * * *